United States Patent [19]

Lawson et al.

[11] Patent Number: 4,607,536

[45] Date of Patent: Aug. 26, 1986

[54] APPARATUS FOR SAMPLING SIMILAR LAMINAR ARTICLES

[75] Inventors: Robert Lawson, Little Chalfont; Malcolm J. Mason; Peter I. Maris, both of St. Albans, all of United Kingdom

[73] Assignee: Baker Perkins Holdings PLC, England

[21] Appl. No.: 577,793

[22] Filed: Feb. 7, 1984

[30] Foreign Application Priority Data

Feb. 11, 1983 [GB] United Kingdom ............... 8303770

[51] Int. Cl.$^4$ .................. B65G 60/00; G01N 1/04
[52] U.S. Cl. ............... 73/863.91; 73/432 R; 414/37; 414/71; 414/744 B
[58] Field of Search ............ 414/71, 72, 744 B, 37; 73/863.91, 864.31, 432 R; 198/486; 271/194, 227, 228

[56] References Cited

U.S. PATENT DOCUMENTS

| | | | |
|---|---|---|---|
| 2,950,829 | 8/1960 | McBean et al. | 414/744 B |
| 3,618,742 | 11/1971 | Blanchard et al. | 198/395 |
| 3,881,356 | 5/1975 | Palm | 73/863.91 |
| 3,921,821 | 11/1975 | Champion et al. | 73/863.91 X |
| 4,117,799 | 10/1978 | Koula et al. | 414/72 X |
| 4,371,159 | 2/1983 | Doyen et al. | 271/228 |

FOREIGN PATENT DOCUMENTS

| | | |
|---|---|---|
| 2068592 | 8/1971 | France . |
| 1154368 | 6/1969 | United Kingdom . |
| 2068870 | 8/1981 | United Kingdom . |
| 493420 | 2/1976 | U.S.S.R. ................. 414/72 |

Primary Examiner—Leslie J. Paperner
Attorney, Agent, or Firm—Lowe, King, Price & Becker

[57] ABSTRACT

The invention relates to apparatus for sampling similar laminar articles, in particular biscuits, on a conveyor. The apparatus comprises photocells (1) for detecting the location of laminar articles (8) on the conveyor (7), an article pick-up suction head (2) positioned downstream of the photocells and in fixed relation thereto, and connections for transmitting a signal from the photocells to the suction pick-up head to actuate the latter when a laminar article is in a predetermined position with respect thereto.

9 Claims, 4 Drawing Figures

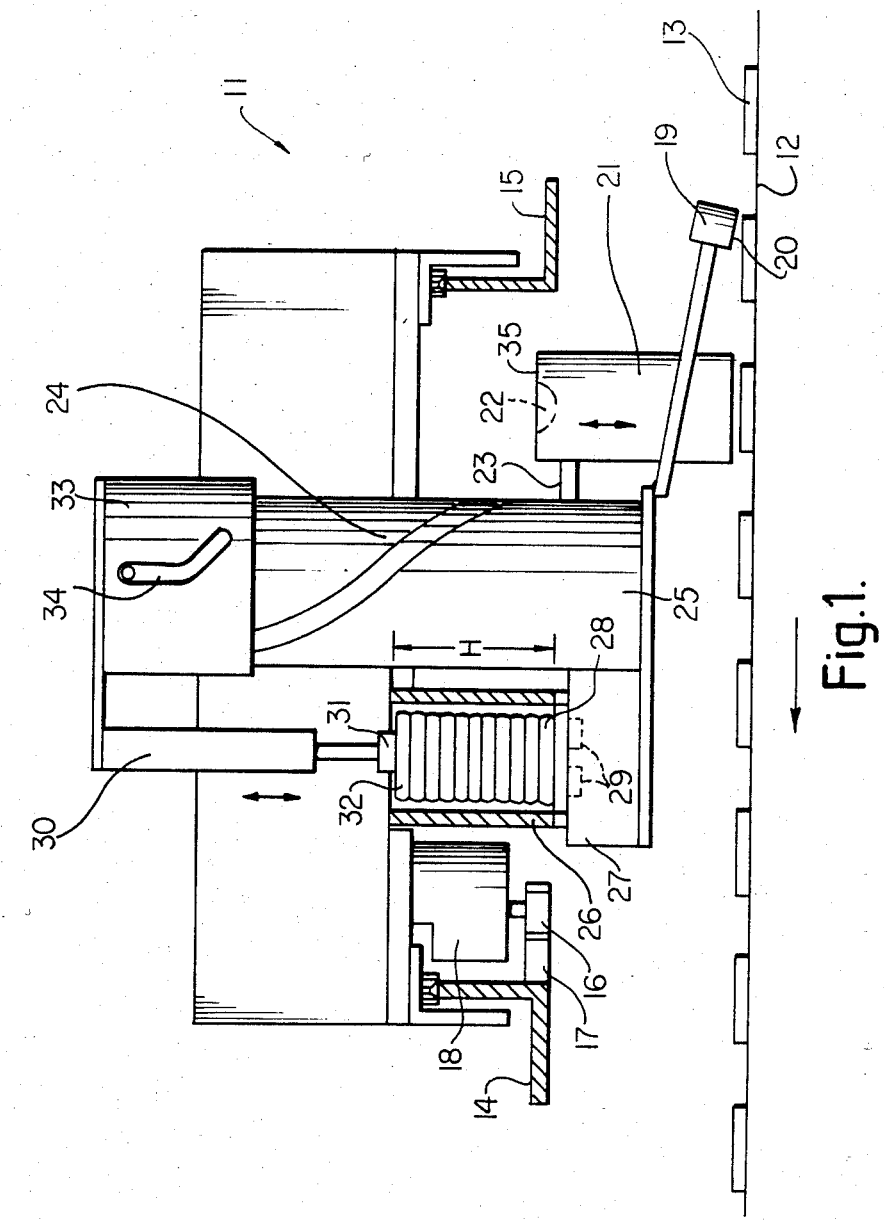

APPARATUS FOR SAMPLING SIMILAR LAMINAR ARTICLES

TECHNICAL FIELD

This invention relates to apparatus for sampling similiar laminar articles. The apparatus is particularly but not exclusively suitable for sampling and recording the dimensions of biscuits.

BACKGROUND OF THE INVENTION

In a modern biscuit baking plant, doughpieces are continuously made, either by extruding dough into a rotary moulder, or by cutting doughpieces from a continuous sheet using reciprocating or rotary cutters. The doughpieces, deposited onto a continuous moving band, are then carried into and through an oven for baking, and emerge therefrom on a conveyor.

Two of the properties of the biscuits which must be continuously and accurately assessed and controlled are their weight and thickness, preferably immediately after leaving the oven. An object of the invention is to measure these two properties automatically at fixed, small intervals of time. It is possible to extend the scope of the apparatus to measure other properties such as crust color and moisture content.

DISCLOSURE OF THE INVENTION

This invention provides apparatus for sampling similar laminar articles on a conveyor, comprising detecting means for detecting the location of laminar articles on the conveyor, article pick-up means, and in fixed relation thereto, and means for transmitting a signal from the detecting means to the pick-up means to actuate the pick-up means when a laminar article is in a predetermined position with respect to the pick-up means.

In the following description, reference is made to biscuits and biscuit baking plants. However, the apparatus is applicable to any plant making a product of comparable size and weight, i.e. laminar in form and preferably light enough to be picked up by suction.

BRIEF DESCRIPTION OF THE DRAWINGS

Reference is now made to the accompanying drawings, in which:

FIG. 1 is a diagramatic side view of apparatus according to a preferred embodiment of the invention.

BEST MODE FOR PRACTICING THE INVENTION

Figure 2A:
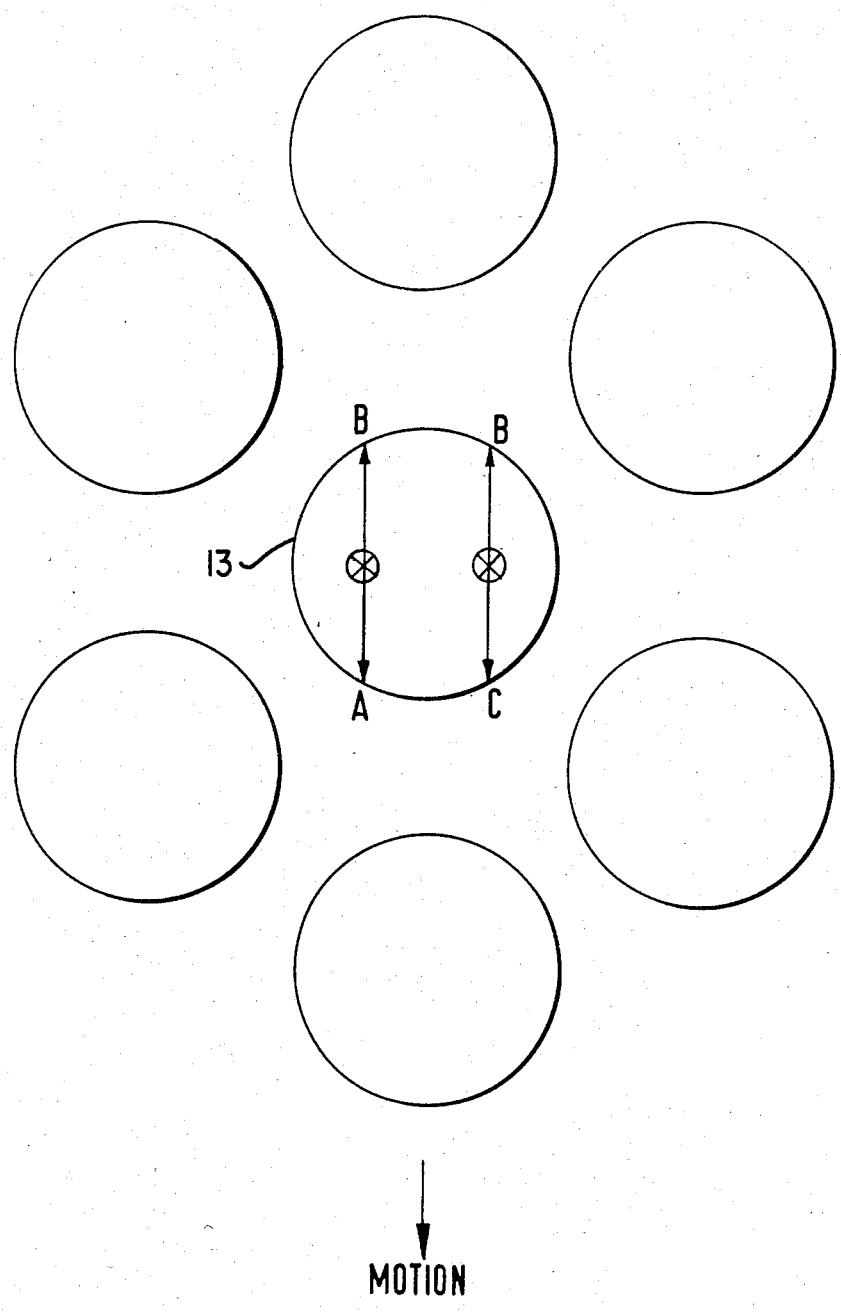
FIG. 2A, 2B, and 2C are plan views of biscuits on a conveyor illustrating the detection of their position by means of photocells.

The apparatus consists of an assembly 11 stationed above the biscuit-carrying band 12 at a point close to the delivery end of the oven, an assembly which has some of the qualities of a robot in that it has the capability of handling biscuits 13 and is programable. It also has the capability of traversing the width of the band 12 so that any file of biscuits 13 can be selected according to a predetermined program. To achieve this capability, the assembly 11 rests on one or more beams 14, 15 fixed transversely across the band, and a rotary member 16 on the assembly engages with a rack 17 attached to one of the transverse beams, i.e., 14. The driving motor 18 for the cross-motion is thus, in this embodiment, an integral part of the assembly 11. In an alternative embodiment, the cross motion is effected by means of a lead screw and nut of conventional form and the driving motor can therefore be mounted externally of the assembly 11 at the side of the band 12.

In order to simplify the description of the operation of the assembly 11 it will be advantageous to assume it to be at a fixed point above the band 12, approximately over one file of biscuits 13. A member 19 fixed to the assembly 11 houses two or more photoelectric cells 20 which are facing downward towards the band 12 and are quite close to it (in the order of 10 to 15 mm). Each cell 20 can thus sense the presence or absence of a biscuit 13 and can accordingly send signals to the controlling computer (also integral with the main assembly but, for simplicity, not shown separately). By this means, two purposes are served: (a) that transverse movements can be given to the assembly 11 in order to keep it centered over the biscuit file, and (b) that the leading or trailing edge of a biscuit 13 can be sensed in order to enable accurate pick-up of a biscuit by pick-up head 21 about to be described.

The pick-up head 21 is a hollow cylinder with its axis vertical. When the pick-up head 21 is fully down, its axis is centered over the same file of biscuits 13 as the sensor assembly 19 and is some distance "downstream" (say 100 mm) thereof. Thus, when the sensors 20 sense the leading edge of a biscuit 13 they sent signals to the computer, which allows for the time necessary for the biscuit 13 to move into a position directly under the pick-up head 21 before sending signals to a solenoid which permits compressed air to enter the pick-up head 21 and initiate suction. Suction set up in the pick-up head 21 then draws up the biscuit 13 and holds it against the lower edge of the pick-up head 21. It is to be noted that contact between the biscuit 13 and the suction head 21 is not necessary for pick-up to occur, and that the pick-up head 21 is entirely stationary during the pick-up operation.

Once a biscuit is picked up, a photocell 22 in the suction head 21 senses the presence of the biscuit 13 and sends a confirmatory signal to the computer. In one embodiment, there are at least two photocells 22 inside the pick-up head 21 so as to give confirmation that the biscuit 14 is accurately positioned with respect to the head. If the head photocell(s) 22 does not give confirmation of a successful pick-up, suction is switched off and a new pick-up cycle is started. If subsequent pick-up attempts are unsuccessful, after a count of (say) eight, the carriage of the assembly 11 is re-aligned over the file of biscuits 13 and further attempts at a pick-up are made.

After a successful pick-up, the computer then sends signals to a motor (not shown for simplicity) which drives a mechanism for raising the pick-up head 21 to its upper position. A laterally positioned arm 23, on which the pick-up head 21 is mounted, engages in a spiral slot 24 in a vertical cylinder 25. As the head assembly in raised, the spiral slot 24 causes the pick-up head 21 to move in an upward spiral path so that when it reaches the highest point, the pick-up assembly has swung through an angle of 180 degrees from its lowest point and has thereby moved a distance downstream of about 300 mm. During this movement the suction is maintained, with the biscuit 13 still in position. The biscuit 13 is now stationed above a stack 26 of (say) ten biscuits resting on a platform 27 to which is attached a set of load cells 29, the output from which gives a signal proportional to the weight of the stack 26 of biscuits. Before the suction is released, the weight of the old stack is read in by the computer. Then the lowest biscuit 28 in the stack 26 is ejected by a pneumatic ram of conventional form and falls down onto the biscuit band 12. The stack 26 is then again weighed and the weight of the diminished stack compared in the computer with the previously recorded weight. If the difference is of such magnitude as to indicate that a whole biscuit has been ejected, the machine moves on to the next stage in the cycle. If the difference indicates that normal ejection has not occurred, the apparatus goes into a "clear down" routine to be described later.

The next state in a normal cycle is for suction at the pick-up head 21 to be switched off. This causes the new biscuit to fall onto the top of the diminished stack, thus restoring it to its normal number. The photocell 22 in the pick-up head 21 is used by the computer to check that the new biscuit has been released and the load cells 29, which are serving as a transducer, take the weight "W" of the stack 26 and calculate that the new biscuit is normal before going on to the next action, which is to switch on and reverse the lifting motor of the pick-up head assembly. The pick-up head 21 thus returns to its lower position ready to pick up the next biscuit in the cycle.

A function of the apparatus which has not so far been described is the measurement of the height "H" of the biscuit stack. This measurement is effected by a transducer which consists of a vertically mounted linear displacement transducer (LDT) 30 having its moving member 31 weighted so as to fall to its lowest position in the absence of restraint. When the pick-up head 21 is down, the moving member 31 of the LDT is able to fall so as to come into contact with the upper surface 32 of the biscuit stack. In this position, the computer is therefore able to read the height "H" of the biscuit stack. The weight transducer 29 is not at this time able to measure biscuit weight "W" of the stack 26 because of the weight of the LDT armature, i.e. moving member 31, resting on it. Advantage of this state is taken to carry out automatic calibration of the weight transducer 29. The LDT armature 31 is made to a given weight so that the weight transducer signal contains two components, a component due to the weight of the stack 26 of biscuits and another due to the known weight of the armature 31. A simple subtraction then enables the computer to compare the known weight of the armature 31 to the load cell signal derived from it and so a spot calibration is achieved for each cycle of the apparatus. An alternative piece of information can be obtained from the weight of the LDT armature 31 if desired. If the weight of the armature 31 is increased to a value which pushes the weight transducer against its stops, a value for weight tare "WT" can be obtained, that is, the signal from the weight transducer 29 corresponding to zero weight on the platform 27. Thus a value for weight tare can be obtained every time a biscuit is changed, instead of once an hour at the clear-down routine as described below.

In order to weight the biscuit slack 26 without the LDT armature 31 resting on it, the LDT assembly 30 can be moved in an upward spiral to an extent sufficient to lift it clear of the biscuit stack 26. The upper movement of the LDT assembly 30 is guided by a cylinder 33 attached thereto and having a spiral slot 34. The lifting is activated by the upward movement of the pick-up head assembly 21. During the later portion of the upward travel of the pick-up head 21, a surface 35 at the top of the pick-up head assembly 21 engages with a corresponding part of the LDT assembly 30 and the LDT is thereafter lifted by the pick-up assembly in a pick-a-back fashion. In other embodiments of the apparatus, other methods of measuring the height of the stack can be used, for example, by optical means in which the lateral movement of a spot of light is used to indicate changes in the height of the surface on which the spot is focussed.

Biscuit weight "W", stack height "H", and any other information measured or calculated by the apparatus can be accessed in two ways, by a digital display on the instrument itself, or at a set of electrical terminals either as analogue or digital signals capable of being connected to a strip-chart recorder or to another computer or to any other external device.

Normal cycling of the apparatus will now be described. The next function to be described has already been referred to as the clear-down routine. This routine normally comes into action once an hour but it can, as already indicated, come into action as the result of a fault occurring. When the clear-down routine is initiated, normal operation is suspended, the pick-up head 21 is lifted to its upper position, and suction is switched off. The biscuit ejecting mechanism is then operated eleven times (assuming there to be ten biscuits on the stack) and between each ejection the weight "W" of the stack 26 checked to ensure that a biscuit has in fact gone. With all biscuits ejected, the surface of the biscuit platform 27 is purged with a jet of air to remove loose crumbs, and the weight read by the computer to reestablish the tare "WT". Thus, the zero weight condition is measured each hour, giving a second calibration check on the weight transducer 29. If the new tare "WT" is too large, it is assumed that part of a broken biscuit has become wedged on the weighing platform 27, and the apparatus goes into a fault routine. If all is in order, the computer initiates the picking up of a new stack 26 of biscuits, the weight of each biscuit 13 being checked as it is loaded, until the required number is reached. What the hourly clear-down routine achieves is:

(a) a clearing of loose crumbs from the weighting platform 27;
(b) a check of the zero weight state (tare) "WT";
(c) a precautionary renewal of the biscuit stack 26 to guard against broken and/or misaligned biscuits, and the possibility of the count of biscuits in the stack having somehow gone wrong.

Of the faults which initiate a clear-down routine, the principal one is when the weight of a new biscuit added to the stack is too small. This is taken to indicate that the new biscuit might be broken or is a seriously deformed or lightweight piece. Another fault would be the converse, a seriously overweight piece, indicating a possible double biscuit. If the photocell detectors 22 indicate that production of biscuits may have stopped, the first half of the clear-down routine is entered, i.e., the stack is emptied but not refilled. The photocells 22 then continue to scan the empty band 12 until fresh biscuits 13 appear and the stack 26 is then recharged.

Figure 2B:
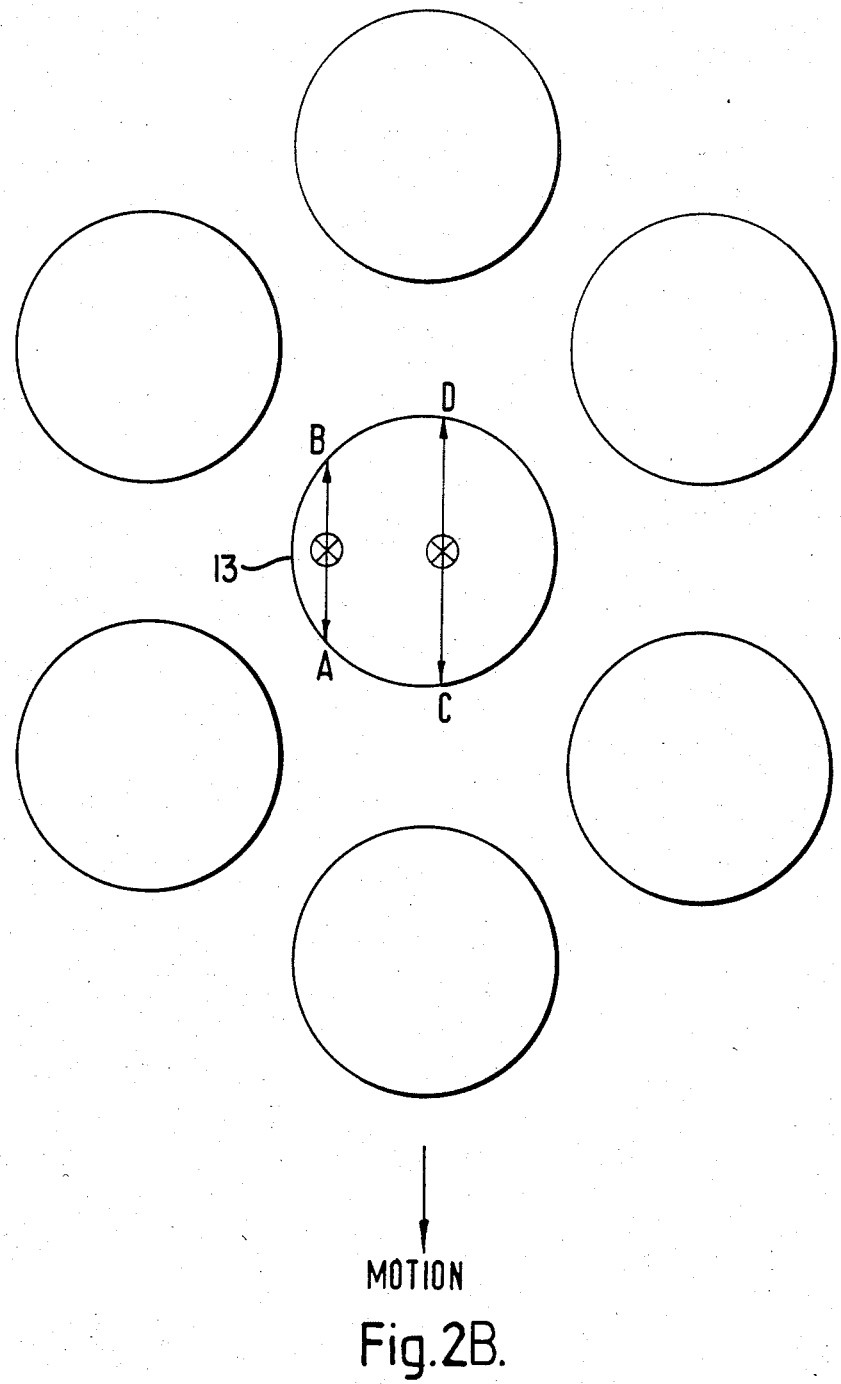
Figure 2C:
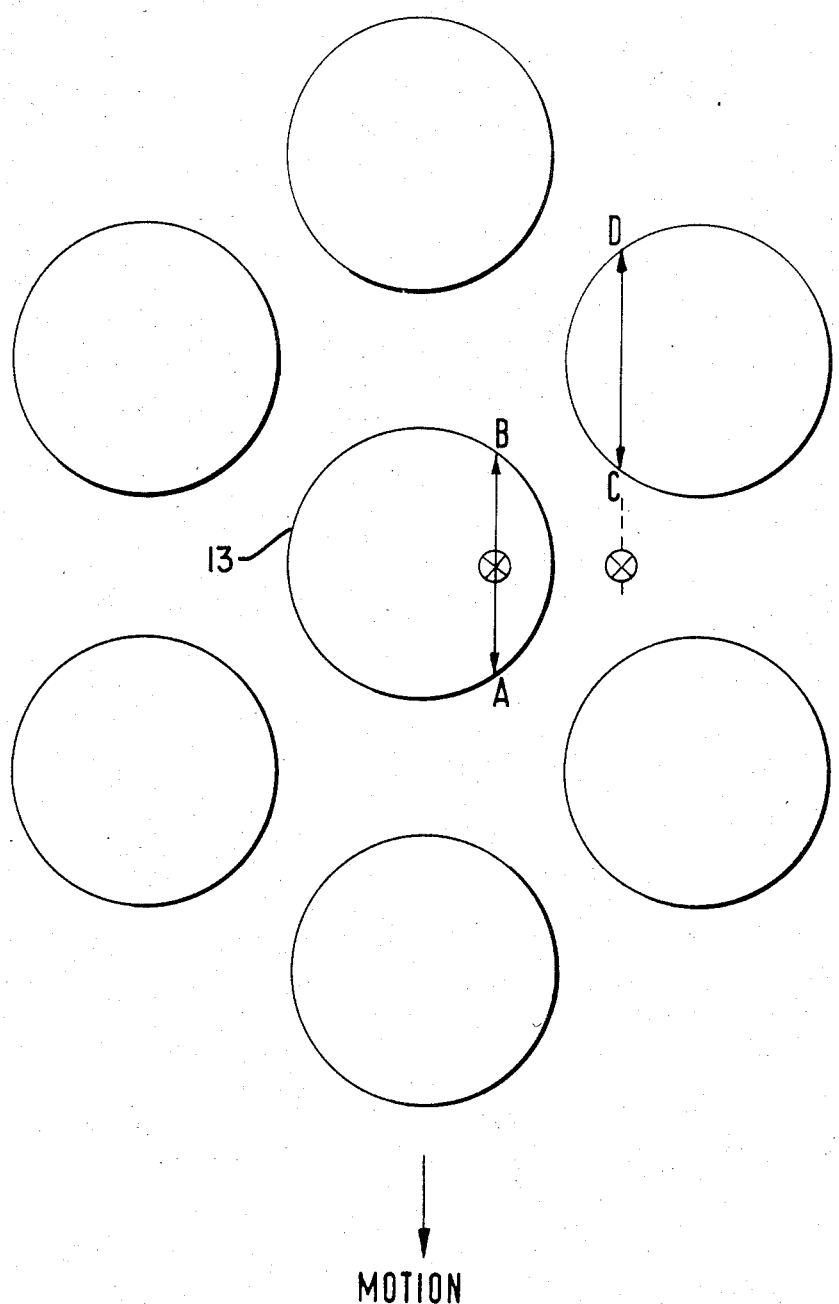

It has already been indicated that transverse location of the apparatus is effected from photocells 22 scanning the biscuits as they pass underneath. The system for detecting the centerline of the biscuits 13 may depend on the shape of the biscuits. From this point of view, the great majority of biscuits fall into two categories: elliptical and rectangular, of which circles and squares are members. In both cases, detection of the center line can be done with the aid of two photocells 22, but the method of detection is different for each category. In the case of elliptical biscuits the transversely mounted photocells, as shown in FIG. 2A, are spaced apart a distance equal to about one third the diameter of the ellipse lying transversely across the band. As the biscuits pass beneath the photocells, they receive "on" signals having durations proportional to chordal lengths of the ellipse. When these lengths are coincident both in extent and in time, the two photocells are exactly straddling the longitudinal center line of the ellipse and no lateral correction is necessary. This is the situation depicted in FIG. 2A. If the left chord is greater that the right, the suction head is right of the biscuit center, and a leftward movement should be initiated in order to correct the error, and vice versa. This is the situation depicted in FIG. 2B. If the chords are equal in length but not coincident in time, as depicted in FIG. 2C, the suction head is exactly above the line between two files of biscuits. In this case the computer is programmed to move either to the left or right for a distance equal to about one third of a biscuit diameter from which position it is able to locate the file center line in the usual way.

In practice, it is not advantageous to initiate sideways movement on information coming from only one biscuit, because the biscuits may not always lie in exactly linear files as they may be subject to random lateral scatter at some point in the process. To meet this condition, the computer is programmed to calculate the average of chordal lengths from eight biscuits before making a move and it then ignores the next eight. This procedure makes for greater stability of the apparatus. A dead-band of about 5 mm also helps to avoid excessive movement of the carriage.

For rectangular biscuits, the photocells are preferably spaced apart an amount equal to half the average lateral distance between the center lines of adjacent files. In operation, one photocell is arranged to sit over the center line of the file which is being scanned. The other photocell will then scan nothing but empty band, and this is taken as the stable position. In practice, the small space between adjacent files will act as a dead band.

The movement of the apparatus across the whole band will now be described. Normally the managers of a biscuit plant require information about the qualities of biscuits from across the whole band rather than from a fixed part of it. To achieve this requirement, the apparatus has mechnical means of driving itself across the whole band, such as a rack an pinion as already mentioned. At each side of the band will be a fixed dog which is able to engage with a microswitch mounted on the assembly and connected electrically to the computer. Alternatively, the dogs and microswitches can be replaced by solid-state proximity switches operating on magnetic, inductive or optical prinicples. These switches give the computer a means of determining with adequate accuracy (say 5 mm) that the assembly has reached one of its limiting positions at the sides of the band. When the apparatus is not operating it will normally stand at one side of the band known as the parking side. When the apparatus receives an instruction to being operation, it will move away from the parking side, keeping a record of distance travelled from the parking position, either by timing its motion, or by the use of a means of measuring lateral position such as a potentiometer geared to the driving motor. As the apparatus moves across the band the photocells 22 will sense the presence of biscuits and will relate the lateral position of biscuit files across the band 12 to the absolute position at which the biscuits are sensed. Thus a map of biscuit files is created in the memory of the computer, which is continually updated.

Permanently stored in the computer will be a program for sampling biscuits across the band. For example, it might be decided that only even files should be sampled both on the outward and inward pass of the apparatus so that, leaving the parking position, files 2,4,6 etc. would be sampled and leaving the other side, files, 20,18,16 etc. would be sampled. Clearly any repetitive sequence of the sort could be programmed. The weight and thickness of the stack as recorded by the apparatus in such circumstances can be analysed in a variety of ways according to management requirements. The simplest method is simply to calculate running means of the stack weight and height. Alternatively, the weight and thickness of each biscuit can be taken separately and used to create a running profile of biscuit weight and stack height across the band. The same information can be used to give a prediction of packet weight, either as a general figure or, in a plant which has two checkweighers, as a separate figure for each half of the band.

As mentioned above, the apparatus has some capability of detecting its own faults. Some of the faults it can check are:

(a) When the pick-up head 21 engages with the stack height measuring mechanism, signals from the stack height transducer 30 can be read by the computer and checked against previous readings to ensure both that the stack height mechanism and transducer are in good order.

(b) When the pick-up head 21 begins to move upwards from its lowest position, a time of one second is allowed to elapse and then the upper and lower limit switches are checked to ensure that they are in a "not operated" state. A similar procedure can be adopted for downward motion. These tests check that the pick-up head 21 does move vertically in response to appropriate signal, and/or that the limit switches are in order.

(c) The times for raising and lowering the pick-up head 21 are compared with expected values to ensure that the appropriate mechanism is in good order.

(d) The stack weights before and after clear down are compared. Any substantial discrepancy indicates either that the old or the new stack was faulty. The apparatus stops operating and displays a fault signal.

(e) Across the band 12, times between biscuit files are used to check that the cross-motion mechanism is in order.

When a fault has been detected, an appropriate signal appears on an indicator panel mounted on the body of the apparatus and all indicators go into a flashing mode to attract attention.

Advantages of the invention include the following features:

(a) An improved method of biscuit pick-up. Suction pick-up is not unkown in the baking industry, but the method described, which is contactless, has not been seen. Other methods of suction pick-up which involve the use of a flexible suction head pressed into contact with the object are not suited to picking up rapidly moving objects with a high degree of positional accuracy.

Non-suction methods of pick-up such as knife edges combined with moving bands are also very difficult to implement in practice with reliability. They also tend to cause excessive disturbance of biscuits from their desired position on the band and can thereby create difficulties further on in the process.

(b) The suction method of pick-up leads logically to an improved method of loading the stack 26. Other methods of pick-up usually lead to a method of loading the stack which imparts a sideways motion to the biscuit, and this can give rise to problems. In particular, it makes sucessful loading from scratch almost impossible. The suction system avoids sideways motion and loading the stack starting with an empty platform becomes easy.

(c) The use of a reflective photocell 22 to detect the leading or trailing edge of a biscuit 13 so as to enable a biscuit to be picked up with longitudinal accuracy by the pick-up head 21.

(d) The use of two reflective photocells 22 to detect the biscuits and to measure the lateral position of the pick-up head in relation of the centre-line of a file of biscuits.

(e) The use of two or more photocells 22 mounted within the pick-up head 21 to determine whether the picked-up biscuit is in a correct relationship to the head.

(f) The ability to clear down the stack 26 at chosen times so as to check the tare "WT" of the weighing system and to clear crumb and defective biscuits.

(g) The use of the armature 31 of the stack height transducer 30 to calibrate automatically the weighing system.

(h) The ability of the apparatus to traverse across the band 12 and, by the use of photocells 22 itemized under (d), to automatically relate the center lines of biscuit files to absolute linear position across the band 12.

What is claimed is:

1. Apparatus for sampling similar laminar articles being transported on a moving conveyor, comprising:

detection means for detecting the locations of a series of said articles being transported on said conveyor past said detection means and generating corresponding detection signals thereby;

article transferring means, cooperating with said detection means, for pick up of said detected articles one at a time at a predetermined rate from said conveyor, for subsequent transfer thereof to a predetermined location;

a collection means at said location, cooperating with said article transferring means, for collecting a predetermined number of said picked up articles transferred thereto by said article transferring means:

collection controlling means, cooperating with said collection means, for periodically returning to said conveyor one of said articles previously transferred thereto in response to the subsequent transfer of each additional article, to control to said predetermined number the articles present at said collection means;

a property measuring means for periodically determining the magnitude of a property of said predetermined number of said articles collected at said collection means and generating a corresponding property measurement signal thereby; and signal processing means for processing said detection signals and said property measurement signals, respectively, and thereby providing a data output signal representing the magnitude of said property of a predetermined number of said articles.

2. Apparatus for sampling similar laminar articles, according to claim 1, wherein:
said first property is the weight of said articles.

3. Apparatus for sampling similar laminar articles, according to claim 1, wherein:
said first property is the height of said articles.

4. Apparatus for sampling similar laminar articles, according to claim 1, wherein:
said article transferring means employs suction, applied from above, to pick up said detected articles one at a time.

5. Apparatus for sampling similar laminar articles, according to claim 4, further comprising:
motion means, responsive to said detection signals, for moving said apparatus relative to said moving conveyor such that said article transferring means is located correctly with respect to said series of said articles for transfer thereof to said collection means.

6. Apparatus for sampling similar laminar articles, according to claim 1, wherein:
said collection controlling means comprises a pneumatic ram to eject the lowermost of a plurality of said articles collected at said collection means, whereby said ejected article is returned to said conveyor.

7. Apparatus for sampling similar laminar articles, according to claim 6, wherein:
said signal processing means compares said magnitude of said measured property with a predetermined magnitude and if said comparison indicates a discrepancy outside a predetermined range then said collection means is cleared of all articles collected thereto, by successive operations of said ram, for recommenced collection of said articles at said collection means.

8. Apparatus for sampling similar laminar articles, according to claim 1, further comprising:
motion means, responsive to said detection signals, for moving said apparatus relative to said moving conveyor such that said article transferring means is located correctly with respect to said series of said articles for transfer thereof to said collection means.

9. Apparatus for sampling similar laminar articles, according to claim 1, wherein:
said detection means comprises a photoelectric cell.

* * * * *